United States Patent [19]

Halstead et al.

[11] 4,221,743

[45] Sep. 9, 1980

[54] HYDROFORMYLATION PROCESS

[75] Inventors: Robert W. Halstead, Houston; John C. Chaty, Seabrook, both of Tex.

[73] Assignee: Union Carbide Corporation, New York, N.Y.

[21] Appl. No.: 703,130

[22] Filed: Jul. 7, 1976

[51] Int. Cl.² ............................................. C07C 45/08
[52] U.S. Cl. .................................. 568/454; 252/431 P
[58] Field of Search ...................... 260/604 HF, 431 P; 252/431 P

[56] References Cited

U.S. PATENT DOCUMENTS

| | | | |
|---|---|---|---|
| 3,520,937 | 7/1970 | Moell et al. | 260/604 HF |
| 3,527,809 | 9/1970 | Pruett et al. | 260/604 HF |
| 3,555,098 | 1/1971 | Olivier et al. | 260/604 HF |
| 3,920,754 | 11/1975 | Wu et al. | 260/604 HF |

*Primary Examiner*—Werren B. Lone
*Attorney, Agent, or Firm*—Reynold J. Finnegan

[57] ABSTRACT

There is described an improved hydroformylation process in which an alpha-olefin is converted to aldehydes by feeding the olefin, carbon monoxide and hydrogen to a homogeneous liquid phase composition containing a catalytic amount of rhodium carbonyl complexed with a triarylphosphine which is provided in an amount greater than that which complexes with said rhodium carbonyl, a substantial amount of condensation products of said aldehydes and said aldehydes. The improvement involves providing a sufficient amount of oxygen to said liquid phase composition whereby to maintain a desired aldehyde productivity during the operation of said process.

1 Claim, No Drawings

HYDROFORMYLATION PROCESS

This invention is concerned with an improvement in the hydroformylation process described in U.S. Pat. No. 3,527,809 issued to R. L. Pruett and J. A. Smith, on Sept. 8, 1970. Broadly speaking, this invention involves providing a sufficient amount of oxygen to the hydroformylation reaction as set forth in the aforementioned patent whereby to maintain a desired aldehyde productivity, such as is characterized in said patent.

The process of that patent involves the production of oxygenated products rich in aldehydes, particularly normal aldehydes, which comprises contacting an alpha-olefin having up to 20 carbon atoms with carbon monoxide and hydrogen in the presence of a catalytic quantity of a complex catalyst consisting essentially of rhodium in complex combination with carbon monoxide and a triorganophosphorous ligand of the group consisting of phosphites and phosphines which possess a $\Delta$ HNP value of at least about 425. There is also provided in the reaction at least two moles of free ligand for each mole of rhodium present. The temperature of the reaction is in the range of from about 50° C. to about 145° C. and the reaction is operated at a total pressure of carbon monoxide and hydrogen of less than about 450 pounds per square inch absolute. The partial pressure attributable to carbon monoxide is no greater than about 75% of the total pressure. As a result, there is formed oxygenated products which are rich in normal aldehydes having one more carbon atom than the alpha-olefin employed in the reaction. The preferred ligand is triphenylphosphine or substituted triphenylphosphine such as, for example, tritolylphosphine. A typical active catalytic species is rhodium hydridocarbonyltris (triphenylphosphine) which has the formula $RhH(CO)[P(C_6H_5)_3]_3$. The process uses an excess of the triorganophosphorous ligand.

The active rhodium catalyst, as is known in recent literature, can be preformed and then introduced into the reaction mixture media, or the active catalyst species can be prepared in situ during the hydroformylation reaction. As an example of the latter, (2,4-pentanedionato) dicarbonylrhodium(I) can be introduced into the reaction medium where, under the operative conditions therein, it reacts with the triorganophosphorous ligand, e.g., triphenylphosphine, to thus form active catalyst such as rhodium hydridocarbonyl-tris(triphenylphosphine).

In Pruett et al's application Ser. No. 683,534, filed May 5, 1976, now U.S. Pat. No. 4,148,830 see British Pat. No. 1,338,237, there is described an improvement on the process described in U.S. Pat. No. 3,527,809. The process of this copending application involves providing in the aforementioned process a liquid phase homogeneous mixture containing a large concentration of condensation products of the aldehyde being produced in the reaction. It was found, quite surprisingly, that such condensation products can be utilized as a solvent in the reaction in large concentrations without adversely affecting the productivity of the reaction. A significant advantage of that process is that it is possible to avoid significant rhodium catalyst losses by the expedient of not having to separate rhodium from a solvent which is alien to the basic reaction system.

The condensation products of the aldehydes are aldol condensation products varying in molecular weight ranging from dimer structures to tetramer structures and greater in terms of molecular weight. To illustrate the kind of condensation products that are feasible from the aldol condensation of butyraldehyde, reference is made to the following discussion:

In the hydroformylation of, for example, propylene, two products are possible, namely normal and iso-butyraldehydes. Since normal butyraldehyde is the more attractive product commercially, high normal/iso ratios of butyraldehydes are desirable. However, the aldehydic products being reactive compounds themselves slowly undergo condensation reactions, even in the absence of catalysts and at comparatively low temperatures, to form high boiling liquid condensation products. Some aldehyde product, therefore, is involved in various reactions as depicted below using n-butyraldehyde as an illustration:

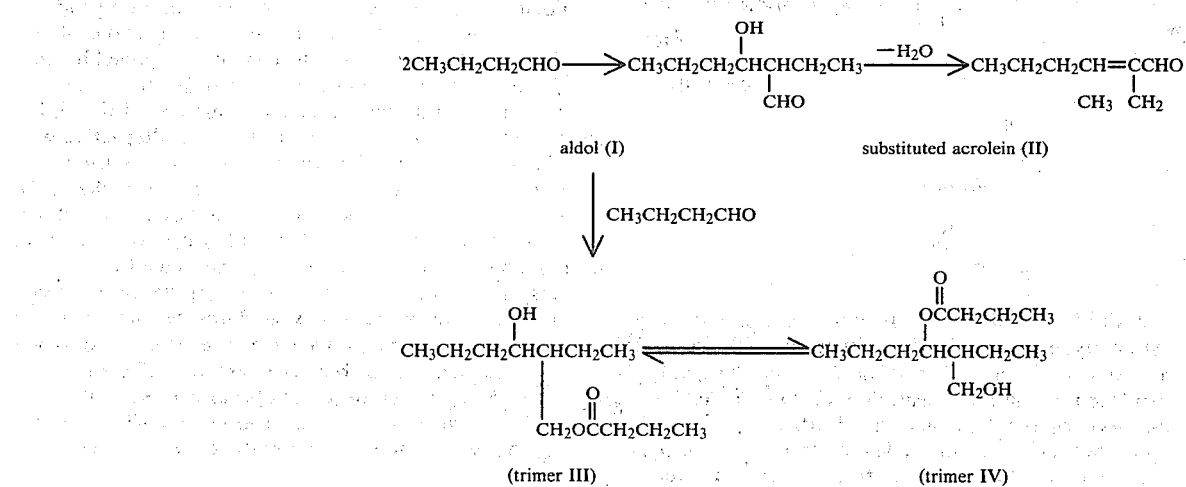

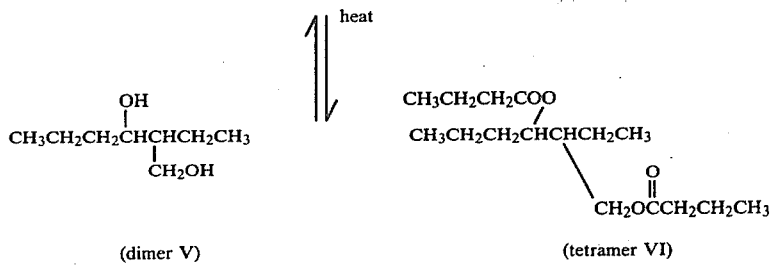

(dimer V)           (tetramer VI)

In addition, aldol I can undergo the following reaction:

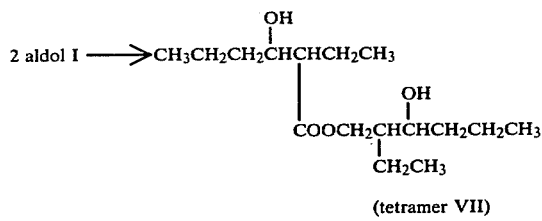

(tetramer VII)

The names in parentheses in the aforeillustrated equations, aldol I, substituted acrolein II, trimer III, trimer IV, dimer V, tetramer VI, and tetramer VII, are for convenience only. Aldol I is formed by an aldol condensation; trimer III and tetramer VII are formed via Tischenko reactions; trimer IV by a transesterification reaction; dimer V and tetramer VI by a dismutation reaction. Principal condensation products are trimer III, trimer IV, and tetramer VII, with lesser amounts of the other products being present. Such condensation products, therefore, contain substantial quantities of hydroxylic compounds as witnessed, for example, by trimers III and IV and tetramer VII.

Similar condensation products are produced by self condensation of iso-butyraldehyde and a further range of compounds is formed by condensation of one molecule of normal butyraldehyde with one molecule of iso-butyraldehyde. Since a molecule of normal butyraldehyde can aldolize by reaction with a molecule of iso-butyraldehyde in two different ways to form two different aldols VIII and IX, a total of four possible aldols can be produced by condensation reactions of a normal/iso mixture of butyraldehydes.

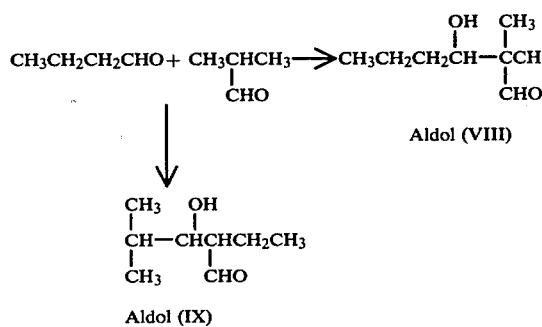

Aldol I can undergo further condensation with isobutyraldehyde to form a trimer isomeric with trimer III and aldols VIII and IX and the corresponding aldol X produced by self condensation of two molecules of isobutyraldehyde can undergo further reactions with either normal or isobutyraldehyde to form corresponding isomeric trimers. These trimers can react further analogously to trimer III so that a complex mixture of condensation products is formed.

It is highly desirable to maintain the substituted acrolein II and its isomers at low concentrations, e.g. below about 5 weight percent. The substituted acrolein II, specifically termed 2-ethyl, 3-propylacrolein ("EPA"), is formed in situ along with other condensation products and has been found to inhibit catalyst activity. The ultimate effect of EPA or like products is to reduce hydroformylation rates to such an extent that any process where the EPA is present in amounts greater than about 5 weight percent, even greater than about one percent by weight based on the weight of the liquid body, will suffer an economic penalty. However, when the alpha-olefin is ethylene, this type of acrolein derivative is not found to adversely affect the catalytic reaction and, therefore, its build-up in the reaction medium is not a critical issue.

In large scale operations utilizing the aforementioned processes, it has been noted that over an extended reaction there is a noticeable drop in the productivity of the process, that is, there occurs a loss of alpha-olefin which is accounted for as the desired aldehyde products or aldehyde derivatives such as the condensation products which build up in forming the homogeneous liquid phase reaction mixture. This can be ascertained by analyzing the off-gas from the reaction for an increase of the alpha-olefin therein, meaning that less of the alpha-olefin is being converted to product. An alternative way of analyzing for a reduction of such productivity would be to maintain a constant concentration of alpha-olefin in the off-gas and decrease the amount of alpha-olefin in the feed to the reaction. When either case occurs, there is a consequent reduction in productivity for the process. Such procedures for ascertaining the productivity of the reaction are typical procedures that are employed to evaluate the performance of the process. It is not intended herein to be bound by any one of these procedures. Any procedure which characterizes an alteration in the productivity of the process is suitable for the purpose of characterizing how that process is performing.

It is difficult to ascertain the reasons for such losses of productivity. It is believed that the catalyst has been rendered less effective. For example, it has been determined in situations where productivity has been decreased, increased additions of catalyst to the reaction only temporarily resolve the lost productivity. Within a relatively short period of time the same loss in productivity initially seen is again found. There is some belief that loss in productivity occurs from the presence of chloride ions in the homogeneous liquid phase mixture. Experience has shown that the aformentioned process does not operate effectively in the presence of chloride ions when provided either as part of the catalyst or independently added with the reactants and/or the catalyst. Other components which could adversely affect the productivity of the process include, by way of example, cyanide and sulfur impurities present in the synthesis gas (the mixture of carbon monoxide and hydrogen), the degradation of the ligand such as triphenylphosphine, and excessive concentrations of the alpha, betaunsaturation such as provided by the substituted acrolein condensation product defined previously as EPA.

There is described herein, a procedure which for one reason or another serves the purpose of either increasing the rate of productivity of the process once the process productivity is decreased, or maintaining a desired rate of productivity to avoid any potential decreases in productivity during the running of the process, or enhancing the rate of productivity over a standard productivity which is considered normal for the process.

To avoid the reduction in productivity which attends the aforementioned process when carried out over extended periods of time, oxygen is added to the homogeneous liquid phase mixture either by directly feeding it to the mixture as air or relatively pure molecular form (i.e. $O_2$) or in admixture with other inert gases, or as part of the synthesis gas feed or in combination with the alpha-olefin which is fed to the reaction. Any other procedure which seems most convenient for the particular reaction system selected may be employed for adding the oxygen. As a result, it is possible to avoid either the loss in rate of production of the aldehyde or maintain a desired productivity of aldehyde; and in certain instances, when desired, increase the production of aldehyde. This is accomplished by simply feeding a sufficient amount of oxygen to the homogeneous liquid phase composition to maintain a desired aldehyde productivity during the operation of the process.

In view of the fact that the process of this invention represents an improvement on the process which is set forth in the aforementioned Pruett and Smith patent and copending application Ser. No. 683,534, now U.S. Pat. No. 4,148,830 the conditions of the reaction as set forth in said patent and application are employable herein and they are incorporated by reference. Specifically, the process of this invention can be operated under the temperature and pressure conditions as stated previously for the process of the aforementioned Pruett and Smith patent utilizing in the liquid phase reaction mixture the aforedefined condensation products, typically present therein in amounts of about 10 to 20 weight percent and greater of the weight of the homogeneous liquid phase reaction composition. In the preferred operation of the process of this invention, the homogeneous liquid phase composition comprises liquid aldehyde products, the liquid condensation products, the triarylphosphine ligands, the dissolved gases and liquid olefin, small amounts of reduced olefin (that is, the parafinic version of the alpha-olefin), the catalyst, and, if desired, other inert liquid materials such as, for example, inert solvents. In the most preferred embodiment of this process, the use of inert solvents other than the condensation products is to be avoided.

It is to be appreciated that this improvement on the aforementioned hydroformylation processes involves the addition of oxygen to the homogeneous liquid phase composition during the operation of the process. In the usual case, it is not necessary to add oxygen when starting up the process. In the typical case, oxygen is fed once the process is under way. However, if one wishes to insure optimum productivity under special circumstances one may include oxygen at the start-up of the process.

The alpha-olefins employable in the process of this invention are those which contain two to about twenty carbon atoms, preferably 2 to about 10 carbon atoms. These alpha-olefins are characterized by a terminal ethylenic carbon-to-carbon bond which may be a vinylidene group, i.e., $CH_2=C<$, or a vinyl group, that is, $CH_2=CH-$. They may be straight-chain or branched-chain and may contain groups or substituents which do not essentially interfere with the course of the novel process. Illustrative alpha-olefins which can be employed as reactants include ethylene, propylene, 1-butene, 2-methyl-1-butene, 1-pentene, 1-hexene, 1-heptene, 1-octene, 2-ethyl-1-hexene, 1-dodecene, 1-octadecene, and the like.

The process is effected in the presence of a catalytically significant quantity of the aforementioned complexed catalyst. The hydroformylation reaction will proceed when employing as little as about $1 \times 10^{-6}$ mole and even lesser amounts, of rhodium (from the complexed catalyst) per mole of alpha-olefin in the feed. Such low catalyst concentrations may be more desirable in the hydroformylation of ethylene. Higher catalyst concentrations are desired for optimum reaction rates with respect to other and higher alpha-olefins. In selecting the minimum catalyst concentrations the relative rates of reactivity of the particular olefin undergoing hydroformylation in conjunction with the catalyst concentration should be considered. The upper catalyst concentration limit can be as high as about $1 \times 10^{-1}$ mole, and higher, of rhodium, per mole of the alpha-olefin feed. However, the upper limit appears to be dictated and controlled more by economics in view of the recognized high cost of rhodium metal and rhodium compounds. No special advantages at such relatively high concentrations are apparent. Therefore, a catalyst concentration of from about $1 \times 10^{-5}$ mole to about $5 \times 10^{-2}$ mole of rhodium metal per mole of alphaolefin feed is typically most desirable. A concentration of about $1 \times 10^{-4}$ to about $1 \times 10^{-2}$ mole of rhodium per mole of alpha-olefin is, in the typical case, most preferred, except with respect to the low catalyst concentrations which can be employed in the hydroformylation of ethylene.

Regardless of whether one preforms the active complex catalyst (e.g., as $RhH[CO][P(C_6H_5)_3]_3$) prior to introduction into the hydroformylation reaction zone or whether the active catalyst species is prepared in situ during the hydroformylation reaction, it is important that the reaction be effected in the presence of free ligand. By "free liquid" is meant the triarylphosphine, as exemplified by triphenylphosphine or alkylated triphenylphosphine, are not tied to or complexed with the rhodium atom in the active complexed catalyst. Another way of stating this is to characterize the amount of triarylphosphine that is present is greater than the amount which complexes with the rhodium carbonyl catalyst. Carbon monoxide, which is also classified a ligand, is present in the catalyst and similarly complexed with the rhodium to provide the active catalytic specie. In some instances, the active catalyst species can also contain hydrogen as a ligand component. It is believed that the preferred embodiment of the catalyst comprises hydrogen, carbon monoxide, and the triarylphosphine as the ligand provided in combination with rhodium to form the active catalytic species. It has been proposed that the active catalyst species is $RhH[CO][P(C_6H_5)_3]_3$.

As pointed out in the aforementioned Pruett and Smith patent and the copending patent application, the process is desirably effected utilizing at least about 2 moles of free triarylphosphine ligand per atom of rhodium contained in the rhodium carbonyl complex catalyst. It is preferred that at least about 10 moles of free ligand per atom of rhodium be employed. The upper limit does not appear to be critical and its concentration is dictated largely by commercial and economic considerations. Frequently, concentrations in excess of 30 moles free ligand per mole of rhodium are employable. The use of large quantities of ligand serves to function as a co-diluent with the aforementioned hydroxylic-containing condensation products.

A feature of the invention as characterized in the patent and in the copending application is the exceptionally low total pressures of hydrogen and carbon monoxide which are required to effect a commercial process. Total pressures of hydrogen and carbon monoxide are less than about 450 psia and as low as 1 atmosphere, and lower, can be employed with effective results. Total pressures of less than about 350 psia and greater than 35 psia are preferred.

The partial pressure of the carbon monoxide has been found to be an important factor in the process. It has been observed that a noticeable decrease occurs in the normal/iso aldehyde product isomer ratio as the partial pressure attributable to carbon monoxide approaches a value of about 75% of the total gas pressure (CO+H$_2$). However, in certain instances, it may be plausible to increase the carbon monoxide partial pressure to a value of above about 75% of the total gas pressure. In general, a partial pressure attributable to hydrogen of from about 25 to about 95% and more, based on the total gas pressure (CO+H$_2$) is suitable. It is generally advantageous to employ a total gas pressure in which the partial pressure attributable to hydrogen is greater than the partial pressure attributable to carbon monoxide, e.g., the hydrogen to carbon monoxide ratio being between 3:2 and 20:1.

Another important variable of the process is the low operative temperatures which can be employed in conjunction with the extremely low pressures and the other well-defined variables. The process can be conducted at temperatures as low as about 50° C. and up to 145° C. with advantageous results. A temperature in the range of from about 50° C. to about 130° C. is preferred.

The concentration of the alpha-olefin can vary over an extremely wide range. For example, one can employ weight ratios of alpha-olefin to complex catalyst between about 1200:1 and about 1:8. However, it must be appreciated that such ratios are merely illustrative and higher as well as lower ratios are clearly contemplated as being within the scope of the invention.

The residence time for the reaction can vary from about a couple of minutes to several hours in duration and, as is well appreciated, this variable will be influenced, to a certain extent, by the reaction temperature, the choice of the alpha-olefin, of the catalyst, of the ligand, the concentration of the ligand, the total synthesis gas pressure and the partial pressure exerted by its components and other factors. As a practical matter the reaction is effected for a period of time which is sufficient to hydroformylate the alpha or terminal ethylenic bond of the alpha-olefin. Of course, ethylene possesses only an alpha ethylenic bond therein and therefore its terminal bond is the same as the alpha positioned bond.

The preparation of the catalyst is thoroughly described in the aforementioned Pruett and Smith application or the corresponding British Patent Specification, and reference is made to them for details of how the catalyst may be prepared.

The hydroformylation process may be conducted in continuous, semi-continuous, or batch fashion. If desired, the catalyst can be added to the hydroformylation zone batchwise, continuous, or incrementally. The aldehyde products can be recovered from the hydroformylation reaction product mixture, for example, by first cooling the effluent from the hydroformylation zone, then passing the same through a let-down valve in which the pressure is substantially reduced, for example, atmospheric pressure. Thereafter, the effluent can be passed through a first long-tube vaporizer to flash off hydrogen, carbon monoxide, unreacted alpha-olefin reactant, etc., at ambient temperature, and then introduced through a second long-tube, which can be maintained at elevated temperature, for example, about 100° C. or less to about 160° C. and higher at about 1 mm. of mercury pressure to about atmospheric pressure (the operative conditions, primarily dependent upon the nature of the aldehyde product of the reaction) to thus strip or recover the aldehydes as an overhead fraction. The liquid residue fraction comprises some unrecovered aldehyde product, free triarylphosphine ligand, high boiling condensation products, and the rhodium values.

As mentioned previously, small amounts of oxygen are provided in the homogeneous liquid phase composition for a variety of purposes. The oxygen can be incorporated for the purpose of maintaining a desired rate of aldehyde productivity or it may be added to overcome a loss in aldehyde productivity or it may be added for the purpose of enhancing the rate of aldehyde productivity over that which is obtainable in the given system by which the process is being conducted. The amount of oxygen which is utilized is not narrowly critical in order to perform these various functions. However, the maximum amount employed should not be so great as to produce an amount of products which would be construed as undesirable products of the hydroformylation reaction and the minimum concentration should not be so little as to be incapable of effecting these aforementioned desired results. Between those functional determinations, the amount of oxygen employed is dependent upon one's experience in the utilization of the process. In some systems, a small amount of oxygen is more beneficial and in other instances a large amount will prove more desirable. Thus, a certain measure of trial and error is necessary in order to ascertain that amount of oxygen which is optimum. In some cases the oxygen may be continuously supplied to the reaction in order to maintain the desired effect and in other cases, the oxygen may be introduced to the reaction on a intermittent or periodic basis in order to provide a select result. Typically, the amount of oxygen which is provided in the process of this invention can range from as little as about 0.004 to about 2 liters of oxygen for each gallon of homogeneous liquid phase composition per hour of process operation. Preferably, the amount of oxygen which is employed in a normal type of operation where sudden changes in the process are not sought would be about 0.01 to about 0.2 liters of oxygen per gallon of homogeneous liquid phase composition per hour of operation. In some instances, the effect sought from oxygen can be achieved by utilizing a very large amount of oxygen over a relatively short period of process operating time. For example, one may utilize amounts ranging from about 0.2 to about 2 liters of oxygen per gallon of homogeneous liquid phase composition per hour of operation for a period of about 24 hours or less to effect a marked alteration in the performance of the catalyst. Most desirably, one would probably operate at those oxygen concentrations for a period of less than about 5 hours of process operation.

When utilizing oxygen under those kinds of conditions one must be careful to avoid the possibilities of detonation occurring by virtue of such a large concentration of oxygen in admixture with olefin and hydrogen as is present in the reaction mixture of the process of this invention. In addition, it is desirable to minimize the amount of iron present in the homogeneous liquid phase composition. It is believed, though not proven, that such iron which is present, is typically present in the form of its pentacarbonyl. Oxygen has the potential of converting such structure into trivalent or divalent iron compounds which have a capacity of converting aldehydes directly into ester alcohol compositions which are characterized herein as the condensation products.

The results achieved by practicing the process of this invention are directly opposite to those which are recited in U.S. Pat. No. 3,555,098, patented Jan. 12, 1971 to Kenneth L. Oliver and Frank B. Booth, assigned to Union Oil Company of California. That patent specifies that the presence of oxygen in the hydroformylation reaction described in that patent acts to oxidize either the aldehyde or the alcohol products of the hydroformylation reaction to carboxylic acid which accumulates during the course of the reaction sufficiently to cause a "detectable decrease in conversion rate", see column 2, line 11 of said patent. Though the differences between the process of this invention and that set forth in the Oliver et al., patent characterize entirely different effects from the addition of oxygen, a careful analysis of the patent gives no explanation as to why the oxygen should behave differently in the process of that patent from the effect which is noted hereinabove when oxygen is incorporated pursuant to the process of this invention. It could be that in the practice of the process of the Oliver et al. patent that there were present during the process, certain ingredients which the patentees fail to characterize. Such non-disclosed components may have been the cause for providing the adverse effect which the patentees characterize when oxygen is provided in the reaction system.

Although this invention has been described with respect to a plurality of details, it is not intended that the invention should be limited thereby. The following examples serve only to characterize the best mode of practicing this invention and it is not intended that such best modes should act to limit the claims.

EXAMPLE 1

The reaction was carried out in the 400 liter reactor which was charged with carbonyltriphenylphosphine-pentane-2,4-dionato rhodium (1)(28.2 g, 40 ppm rhodium metal), 2-methylpentane-1,3-diol monopropionate (123.5 kg., 77.7 percent), propionaldehyde (13.6 kg., 8.6 percent), and triphenylphosphine (21.7 kg., 13.7 percent). The reaction mixture was treated with a mixture of ethylene (25 psi), carbon monoxide (40 psi), and hydrogen (70 psi), at a total pressure of 200 psig and the reaction rate monitored by the production of propionaldehyde. During the next 1100 hours of operation, substantial declines in catalyst activity were observed and an additional 32.8 gm. of catalyst complex was added to the reaction mixture to maintain aldehyde productivity. On the 46th day of operation, oxygen was added to the gas mixture and hence, to the reactor, at the rate of 0.024 liters per liter of reaction solution per hour. The reaction rate increased as a consequence of the oxygen addition from 335 moles per hour of propionaldehyde to 832 moles per hour of aldehyde. In addition, the ethylene pressure in the reacting gas had dropped from approximately 25 psi down to approximately 3.5 psi. The data clearly showed the beneficial effect of adding oxygen to the hydroformylation mixture.

EXAMPLE 2

The solution used for this example was identical to the solution used for Example 1 with the exception that 75 gm. of the rhodium complex was added to the reactor solution. A gas mixture of approximately the same composition was passed through the reactor solution and shortly after initiation of the reaction, catalyst deactivation was observed. For example, on the first day of operation, the production of propionaldehyde was 762 moles per hour and by the third day of operation the production had fallen to 553 moles per hour and the pressure of ethylene had risen from 5.2 to 36 psi. The oxygen level during this time ranged from 0.001 liters per liter of reactor solution per hour to 0.004 liters per liter of reactor solution per hour. On the fourth day of operation, the oxygen content of the gas was increased to a feed rate of 0.028 liters per liter of reactor solution per hour and the production of aldehyde immediately responded, reaching, by the fifth day of operation, a production rate of 765 moles per hour at an outlet ethylene concentration of 4.1 psi. When the oxygen feed rate was reduced to 0.009 liters per liter of reactor solution per hour there was no further evidence of catalyst deactivation.

EXAMPLE 3

The reaction was carried out in the 400 liter reactor charged with carbonyltriphenylphosphinepentane-2,4-dionato rhodium (1), (228 gm, 275 ppm rhodium metal), triphenylphosphine (13.6 kg. 7.5 weight percent), butyraldehyde (26.4 kg. 16.2 weight percent) and 2-ethylhexane-1,3-diol monobutyrate (122.8 kg. 75.6 weight percent). The reactor was maintained at temperatures of 100° to 120° C. and 175 psig of pressure and maintained under propylene (35 psig), carbon monoxide (10 psi), and hydrogen (80 psi). The initial production rate observed was 384 moles per hour. After extended operation (approximately 1700 hours) the production fell to 145 moles per hour. Oxygen was fed to the catalyst solution over an 80 hour period at a rate of about 0.01 liters per liter of catalyst solution per hour and the productivity of aldehyde increased to a maximum of 421 moles per hour. When the oxygen feed was terminated the aldehyde production rapidly declined to 250 moles per hour.

EXAMPLE 4

The solution used for this example is identical to that used in Example 3. The initial rate observed for the new catalyst solution was approximately 423 moles per hour of mixed butyraldehydes and during the next 250 hours of operation, the productivity gradually fell to 257 moles per hour. Oxygen was introduced at a rate of 0.005 liters per liter of solution per hour and during the next four days the same amount of air was fed and during this time production increased to 319 moles per hour of mixed butyraldehydes. When the air feed was terminated the productivity gradually declined to 261 moles per hour.

For the examples cited number 5 thru 7, the reactions were carried out in a 4-liter stainless steel autoclave equipped with a disperser-type agitator, a gas inlet tube below the liquid level and a gas outlet tube at the top of the reactor. The reactor was heated using an external electrical resistance heater. The reactions were performed at 200 psig total pressure, the pressure being maintained by a motor valve in the gas exit line. Concentrations of the components in the gas were determined by gas chromatographic analysis of samples regularly removed from the gas exit line. The product aldehyde was removed continually by a purge of the reacting gases. The aldehyde production was calculated from the known concentration of aldehyde and volume of exiting gas.

EXAMPLE 5

Dicarbonylpentanedione rhodium (1) (0.416 gm, 275 ppm Rh), triphenylphosphine (45 gm, 7.5 weight percent), normal butyraldehyde (60 gm, 10 weight percent) and 2,2,4-trimethylpentane-1,3-diol monoisobutyrate (495 gm, 82.5 weight percent) were mixed and heated to 110° C. A gas mixture consisting of propylene 44 psi, hydrogen (60 psi), carbon monoxide (24 psi) and nitrogen (61 psi) was maintained in the reactor. An aldehyde production rate of 3.2 moles per hour was observed. Upon the addition of 0.58 liters per liter of reactor solution per hour of oxygen to the feed gases the rate of aldehyde productivity increased to 4.2 moles per hour after two hours.

EXAMPLE 6

Dicarbonylpentanedione rhodium (1) (0.416 gm, 275 ppm Rh), triphenylphosphine (90 gm, 15 weight percent), normal butyraldehyde (60 gm, 10 weight percent) and 2,2,4-trimethylpentane-1,3-diol monoisobutyrate (450 gm, 75 weight percent) were mixed and heated in the reactor to 110° C. A gas mixture consisting of propylene (41 psi), hydrogen (61 psi), carbon monoxide (22 psi), and nitrogen (61 psi) was maintained in the reactor. An aldehyde production rate of 2.6 gm mole per hour was observed. Upon the addition of 0.44 liters per liter of reactor solution per hour of oxygen to the feed gases, the rate of aldehyde production increased to 4.0 moles per hour after 18 hours.

EXAMPLE 7

Chlorocarbonylbistriphenylphosphine rhodium (1) (1.11 gm, 275 ppm of Rh) triphenylphosphine (5 gm, 7.5 weight percent), normal butyraldehyde (60 gm, 10 weight percent) 2,2,4-trimethylpentane-1,3-diol monoisobutyrate (495 gm, 82.5 weight percent) were mixed and heated in the reactor at 110° C. A gas mixture consisting of propylene (44 psi), hydrogen (66 psi), carbon monoxide (26 psi) and nitrogen (61 psi) was maintained in the reactor; no aldehyde reaction was observed. Upon the addition of 0.63 liters per liter of reaction solution per hour of oxygen to the feed gases, a production rate of 2.7 gm moles per hour of aldehyde was observed after 3 hours.

What is claimed is:

1. In the process of hydroformylating an alpha-olefin to produce aldehydes therefrom comprising feeding said olefin, carbon monoxide and hydrogen to a homogeneous liquid phase composition, containing a catalytic amount of rhodium carbonyl complexed with a triarylphosphine present in an amount greater than that amount which complexes with said rhodium carbonyl, an amount of condensation products of said aldehydes, preferably a substantial amount, and said aldehydes, wherein the rate of production of said process in said liquid phase composition can decrease, wherein the improvement which comprises feeding a sufficient amount of oxygen to said liquid phase composition during hydroformylation to maintain a desired aldehyde productivity.

* * * * *